(12) United States Patent (10) Patent No.: US 8,798,749 B2
Maskara et al. (45) Date of Patent: Aug. 5, 2014

(54) CARDIAC STIMULATION DEVICE FOR SINUS RATE MODULATION

(75) Inventors: Barun Maskara, Blaine, MN (US);
Jiang Ding, Maplewood, MN (US);
Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1837 days.

(21) Appl. No.: 11/610,821

(22) Filed: Dec. 14, 2006

(65) Prior Publication Data

US 2008/0147138 A1 Jun. 19, 2008

(51) Int. Cl.
*A61N 1/365* (2006.01)

(52) U.S. Cl.
USPC .......................................................... 607/18

(58) Field of Classification Search
USPC .......................................................... 607/18
See application file for complete search history.

(56) References Cited

U.S. PATENT DOCUMENTS

| 4,773,401 | A | 9/1988 | Citak et al. |
| 5,342,406 | A | 8/1994 | Thompson |
| 6,076,015 | A | 6/2000 | Hartley et al. |
| 6,666,826 | B2 | 12/2003 | Salo et al. |
| 6,928,320 | B2 | 8/2005 | King |
| 2004/0127792 | A1 | 7/2004 | Siejko et al. |
| 2006/0206159 | A1* | 9/2006 | Moffitt et al. .................. 607/37 |

OTHER PUBLICATIONS

Berne, Robert M., et al., "Electrical Activity of the Heart", *Cardiovascular Physiology.*, St. Louis : Mosby, Seventh Edition,(1997), 27-30.
Kane, et al., "Implantable Medical Device With Chemical Sensor and Related Methods", U.S. Appl. No. 11/383,933, filed May 17, 2006, 68 pgs.
Lei, L., et al., "Bradycardia induces angiogenesis, increases coronary reserve, and preserves function of the postinfarcted heart", *Circulation*, 110(7), (Aug. 17, 2004), 796-802.
Shattock, M., et al., "Pure Heart Rate Reduction: The If Channels From Discovery to Therapeutic Target", *BR J Cardiol.*, 13(1), http://www.medscape.com/viewarticle/525569, (2006), 27-35.
Shinke, T., et al., "Beneficial effects of heart rate reduction on cardiac mechanics and energetics in patients with left ventricular dysfunction", *Jpn Circ J.*, 63(12), (Dec. 1999), 957-64.
Zheng, W., et al., "Bradycardia-induced coronary angiogenesis dependent on vascular endothelial growth factor", *Circ Res.*, 85(2), (Jul. 23, 1999), 192-8.

* cited by examiner

*Primary Examiner* — Eric D. Bertram
(74) *Attorney, Agent, or Firm* — Schwegman, Lundberg & Woessner, P.A.

(57) ABSTRACT

A system comprising an implantable electrical cardiac signal sensing circuit, an implantable sinoatrial cardiac action potential detector circuit, and an implantable electrical stimulation circuit in electrical communication with the electrical cardiac signal sensing circuit and the sinoatrial cardiac action potential detector circuit. The electrical cardiac signal sensing circuit is configured to receive one or more intrinsic heart signals from one or more respective electrodes configured for placement in a vicinity of a sinoatrial node of a subject. The implantable electrical stimulation circuit is configured to initiate delivery of at least one inhibitory electrical stimulation pulse in a vicinity of the sinoatrial node in a timed relationship to a sensed sinoatrial cardiac action potential. Other systems and methods are disclosed.

19 Claims, 10 Drawing Sheets

CARDIAC STIMULATION DEVICE FOR SINUS RATE MODULATION

TECHNICAL FIELD

The field generally relates to implantable medical devices and, in particular, but not by way of limitation, to systems and methods for adjusting heart rate.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. CFM devices are typically used to treat patients using electrical or other therapy. They can also help a physician or caregiver in diagnosing a patient by internal monitoring of the patient's condition. CFM devices may include one or more electrodes in communication with one or more sense amplifiers to monitor electrical heart activity within a patient. CFM devices often include one or more other physiological sensors to monitor one or more other internal patient parameters. Other examples of implantable medical devices include implantable diagnostic devices, implantable drug delivery systems, or implantable devices with neural stimulation capability.

Additionally, some IMDs detect events by monitoring intrinsic electrical heart activity signals. CFM devices may also measure one or more hemodynamic parameters, for example, related to heart chamber filling and contractions. Ischemia occurs when blood flow to cardiac muscles decreases below the metabolic needs of the heart. Ischemia impairs the pumping function of the heart. Increased heart rate may be a risk factor for patients who have experienced ischemia. Drug therapy may reduce heart rate but the use of drugs may be limited by negative effects or contraindications.

SUMMARY

This document discusses, among other things, systems, devices, and methods for adjusting heart rate. A system example includes an implantable electrical cardiac signal sensing circuit, an implantable sinoatrial cardiac action potential detector circuit, and an implantable electrical stimulation circuit in electrical communication with the electrical cardiac signal sensing circuit and the sinoatrial cardiac action potential detector circuit. The electrical cardiac signal sensing circuit is configured to receive one or more intrinsic heart signals from one or more respective electrodes configured for placement in a vicinity of a sinoatrial node of a subject. The implantable electrical stimulation circuit is configured to initiate delivery of at least one inhibitory electrical stimulation pulse in a vicinity of the sinoatrial node in a timed relationship to a sensed sinoatrial cardiac action potential.

A method example includes sensing an intrinsic electrical cardiac signal using an implantable medical device (IMD). The cardiac signal is representative of a depolarization at a sinoatrial node region of a subject. The method example also includes reducing a rate of sinoatrial depolarizations by delivering at least one inhibitory electrical stimulation pulse in a vicinity of the sinoatrial node, using the IMD, in a timed relationship to the sensed depolarization.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

Figure 1:
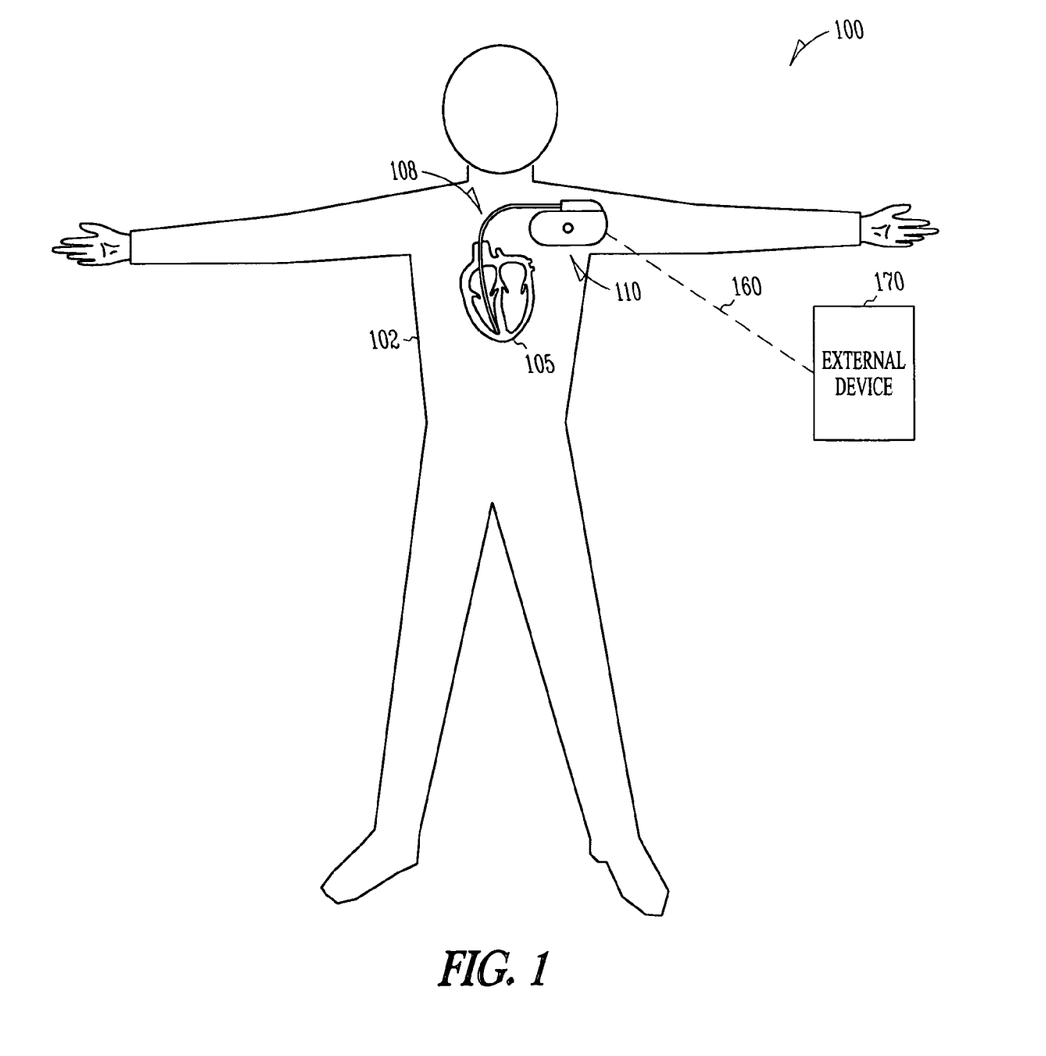
FIG. 1 is a block diagram of portions of a system that uses an implantable medical device (IMD).

FIG. 1 is a block diagram of portions of a system 100 that uses an implantable medical device (IMD) 110. As one example, the system 100 shown can be used to treat a cardiac arrhythmia. The IMD 110 typically includes an electronics unit, which can be coupled by a cardiac lead 108, or additional leads, to a heart 105 of a patient 102 or subject, or otherwise associated with the heart 105. Examples of IMD 110 include, without limitation, a cardiac function management (CFM) device, such as a pacemaker, a cardioverter, a defibrillator, a cardiac resynchronization therapy (CRT) device, or other cardiac monitoring or therapy delivery devices, such as cardiac devices that include or work in coordination with neuro-stimulating devices, drugs, drug delivery systems, or other therapies. System 100 also typically includes an MD programmer or other local and/or remote external device 170 that communicates wirelessly 160 with the IMD 110, such as by using radio frequency (RF) telemetry or another communication signal.

The cardiac lead 108 generally includes a proximal end that is coupled to IMD 110 and a distal end that is coupled by one or more electrodes to one or more portions of a heart 105.

The electrodes typically deliver one or more of cardioversion, defibrillation, pacing, or resynchronization therapy, or combinations thereof to at least one chamber of the heart 105. The electronics unit of the IMD 110 typically includes components that are housed or enclosed in a hermetically-sealed canister or "can." Other electrodes may be located on the can, or on an insulating header extending from the can, or on other portions of IMD 110, such as for providing pacing energy, defibrillation energy, or both, for example, in conjunction with one or more of the electrodes disposed on or around a heart 105. The lead 108 or leads and electrodes may also typically be used for sensing intrinsic or other electrical activity of the heart 105.

The IMDs may be configured with a variety of electrode arrangements, including transveous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). For example, the electrodes need not include an intravascular leadwire, but may instead involve far-field sensing or energy delivery.

Figure 2:
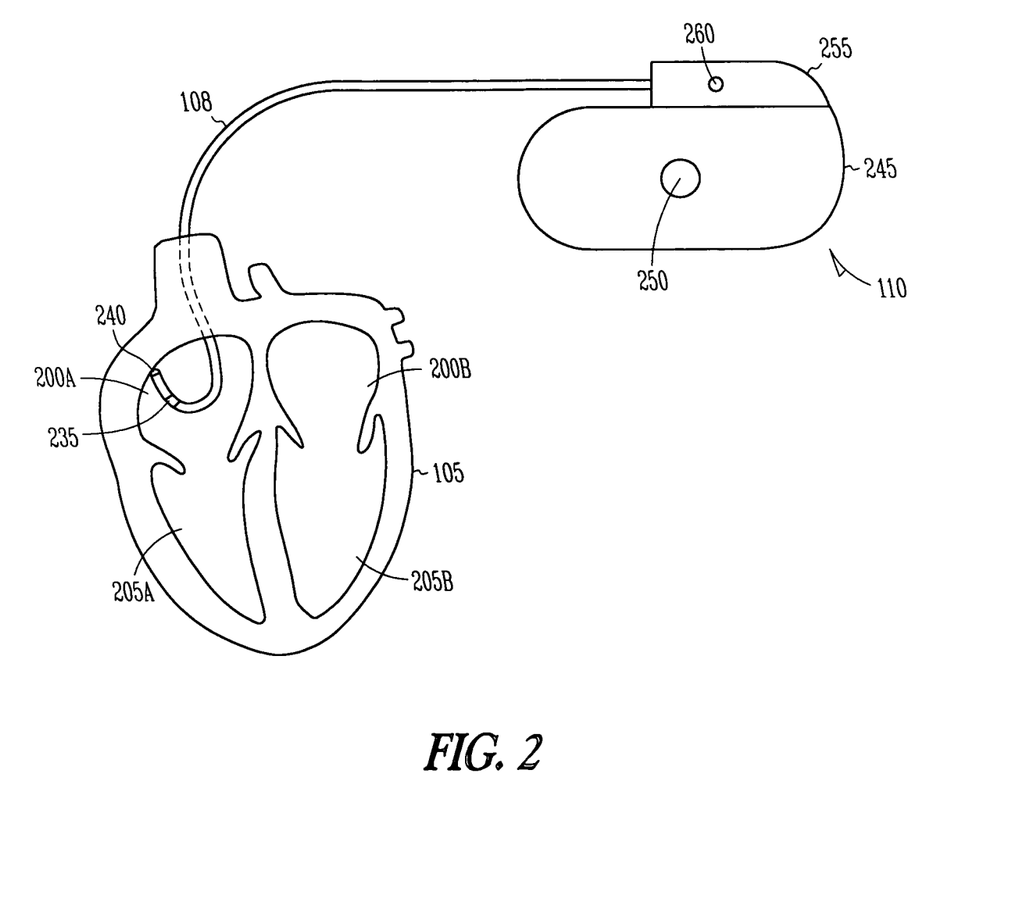
FIG. 2 illustrates an IMD coupled by one or more leads to a heart.

FIG. 2 illustrates an IMD 110 coupled by one or more leads 108 to a heart 105. The heart 105 includes a right atrium 200A, a left atrium 200B, a right ventricle 205A, and a left ventricle 205B. In this example, the lead 108 has a "J" shape for placement high in the right atrium. The lead 108 includes electrodes (electrical contacts, such as ring electrode 235 and tip electrode 240) disposed high in a right atrium 200A of heart 105, such as for signal sensing, or delivering pacing therapy, or both, to or from the right atrium 200A. In some examples, the IMD 110 includes a second lead (not shown) having electrodes for placement in the right ventricle 205A for electrical cardiac signal sensing, delivering pacing therapy, or both signal sensing and delivering pacing therapy. The IMD 110 can adjust timing of the heart chamber contractions. For example, IMD 110 can adjust the timing of ventricular contractions with respect to the timing of atrial contractions delay by sensing a contraction in the right atrium 200A and pacing the right ventricle 205A at the desired atrial-ventricular (AV) delay time. The IMD may also include can electrode 250 formed on the IMD can 245, and header electrode 260 formed on the IMD header 255.

The IMD 110 optionally also includes additional leads and electrodes, such as for delivering atrial cardioversion, atrial defibrillation, ventricular cardioversion, ventricular defibrillation, or combinations thereof to heart 105. Defibrillation electrodes typically have larger surface areas than pacing electrodes in order to handle the larger energies involved in defibrillation. Optionally, lead 108 includes two leads containing two or more electrodes each. In an example, a first lead includes a tip electrode located in the apex of the right ventricle 205A and a first ring electrode located proximal to the tip electrode. A second lead includes a tip electrode located in the right atrium 200A and a ring electrode located in the right atrium 200A proximal to the tip electrode.

Optionally, IMD 110 includes an additional cardiac lead that includes one or more ring electrodes, such as for placement in a coronary vein extending along a wall of the left ventricle 205B. A lead placed in the left ventricle 205B and a lead placed in the right ventricle 205A may be used to optionally provide biventricular pacing or other resynchronization therapy to the heart 105.

Figure 3A:
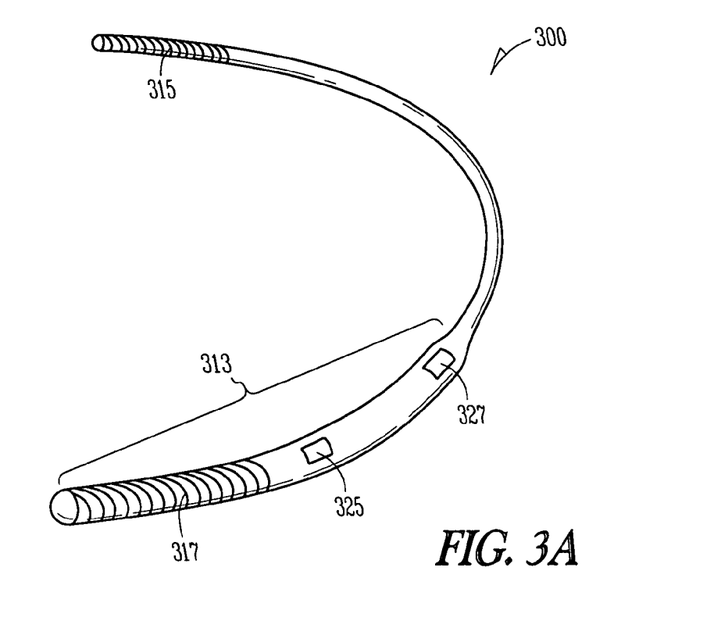
FIGS. 3A and 3B show an example of an IMD that does not use intravascular leads to sense cardiac signals.
Figure 3B:
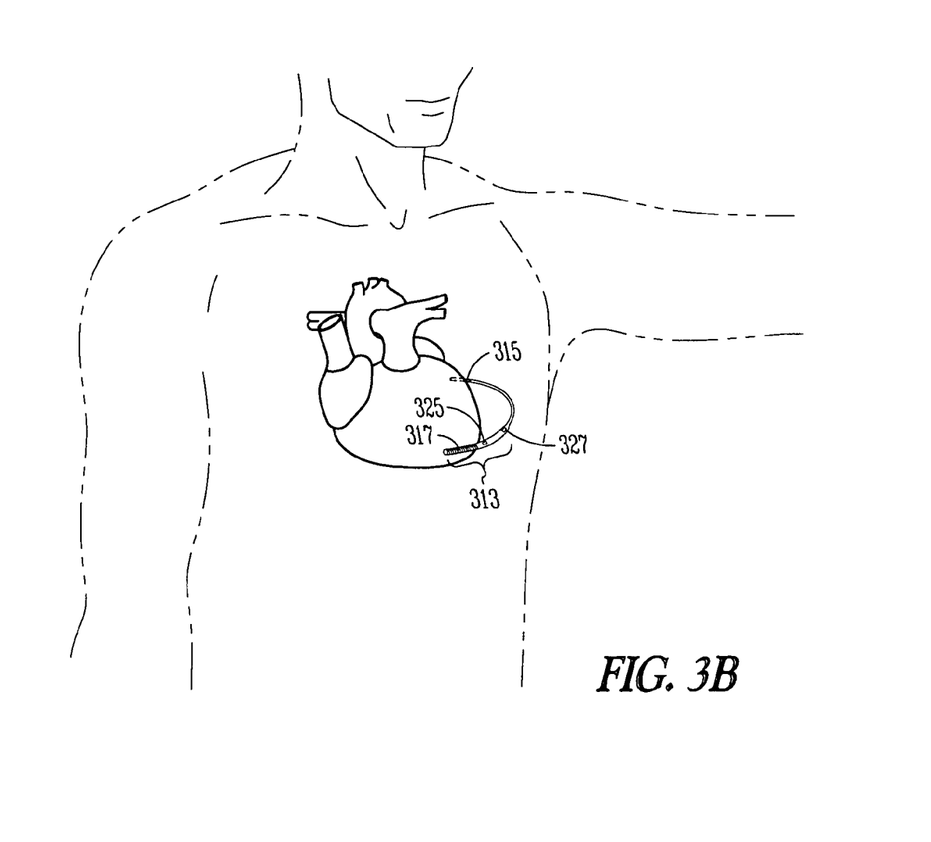

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrodes. FIGS. 3A-B show an example of an IMD 300 that does not use intravascular leads to sense cardiac signals. FIG. 3A shows that the IMD 300 includes a thicker end 313 to hold the power source and circuits. The IMD 300 also includes electrodes 325 and 327 such as for remote far-field sensing of cardiac signals. Cardioversion/defibrillation is typically provided through electrodes 315 and 317. FIG. 3B shows an example of the IMD 300 positioned within a patient. An IMD may include one or more of the features, structures, methods, or combinations described herein.

The spontaneous depolarization of cells of a heart is sometimes referred to as automaticity. This natural pacemaker mechanism of spontaneous depolarization typically originates at the sinoatrial node, where the cells spontaneously depolarize the earliest. The electrical waveform associated with the cell depolarization is typically referred to as a cardiac action potential. Action potentials from cell depolarizations at the sinoatrial node typically propagate from the sinoatrial node through the heart's electrical conduction system to excite various regions of myocardial tissue into depolarizing. The propagating action potentials trigger cell depolarizations that result in mechanical heart contractions during systole repolarizations that result in heart chamber expansion during diastole.

Figure 4A:
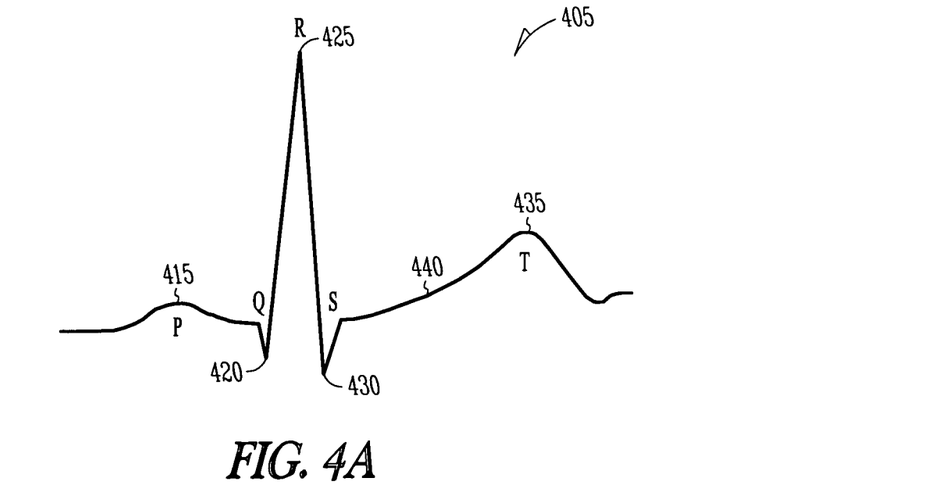
FIG. 4 is an illustration of a P-QRS-T segment of an electrocardiogram (ECG) waveform and a cardiac action potential of a ventricular myocyte.
Figure 4B:
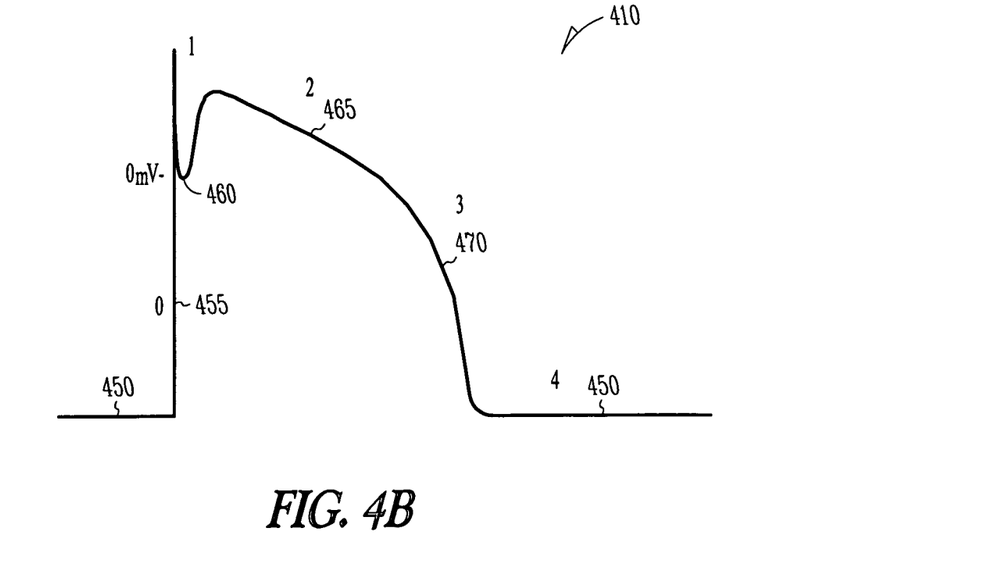

FIG. 4 is an illustration of a P-QRS-T segment of an electrocardiogram (ECG) waveform 405 and a cardiac action potential 410 of a ventricular myocyte. Depolarization of the atrial muscle fibers may be referred to as a P-wave 415. Depolarization of the ventricular muscle fibers may be collectively represented by a Q-wave 420, R-wave 425, and S-wave 430, which form a QRS complex. The portion of the waveform representing repolarization of the ventricular muscle fibers may be referred to as a T-wave 435.

A cardiac action potential 410 of a ventricular myocyte can be divided into five phases numbered zero to four. Phase four 450 is the resting phase of the action potential and is associated with diastole. Phase zero 455 is the phase of rapid cell depolarization and is due to rapid influx of sodium ions ($Na^+$) into the cell. During phase one 460, the rate of sodium influx decreases. An outflux of potassium ions (K+) results in the notch in the cardiac action potential 410. Phase zero 455 and phase one 460 correspond to the QRS complex. Phase two 465 includes a substantial "plateau" of the cardiac action potential 410. The plateau is due to a balance of an outward flow of $K^+$ ions and an inward flow of calcium ($Ca^{2+}$) ions. Phase two 465 corresponds to the S-T segment 440 of the ECG waveform 405. Phase three 470 includes the cell repolarization and corresponds to the T-wave 435 on the ECG waveform 405. The repolarization is due to a net outward positive current from the cell.

Figure 5:
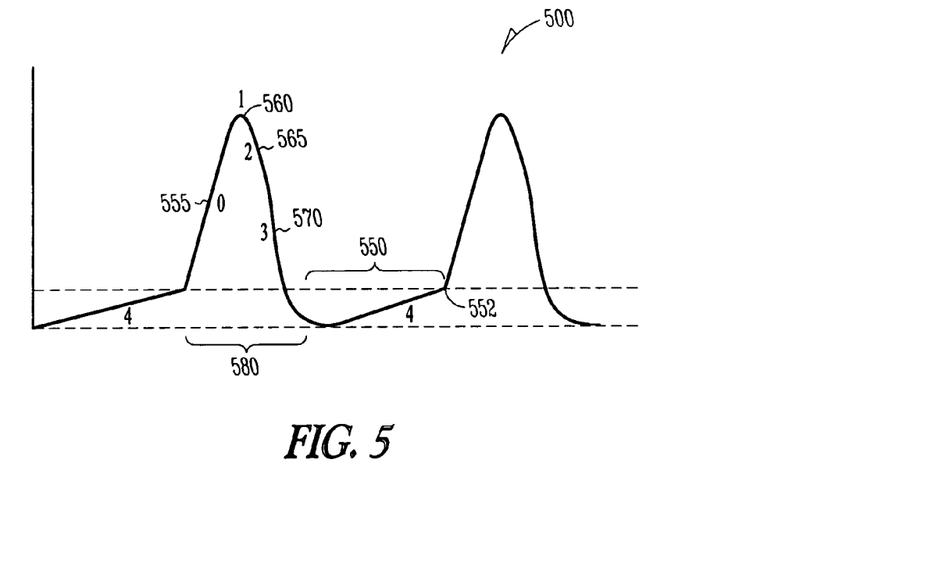
FIG. 5 is an illustration of a sinoatrial cardiac action potential.

FIG. 5 is an illustration of a sinoatrial cardiac action potential 500, e.g., a cardiac action potential at the sinoatrial node. The myocardial cells of the sinoatrial node discharge rhythmically to provide a natural pacemaker mechanism to cause spontaneous depolarization of the cells of a heart. The sinoatrial cardiac action potential 500 typically exhibits a different shape than the ventricular action potential. Phase zero 555 is not as rapid as it is in the ventricle, and phase two 565 does not exhibit as much of a plateau. Phase four 550 of the sinoatrial cardiac action potential 500 is sometimes referred to as a "pre-potential." After the repolarization during phase three 570, there is a slow depolarization during phase four 550. When the pre-potential reaches a firing threshold level 552, depolarization associated with phase zero 555 occurs. As an example, the firing threshold level 552 may be about −40 millivolts (mV). The depolarization is mostly due to an influx of $Ca^{2+}$ ions and smaller influx of $Na^+$ ions, which causes the less-rapid phase zero 555.

Phase zero 555, phase one 560, phase two 565, and phase three 570 cumulatively comprise a cardiac refractory period 580 for an action potential 500. The cardiac refractory period 580 may be separated into an absolute refractory period and a relative refractory period. During the absolute refractory period, a new action potential cannot be started. During the relative refractory period, a new action potential can be started, but only under the correct conditions. The latter part of phase three 570 includes the relative refractory period.

Figure 6A:
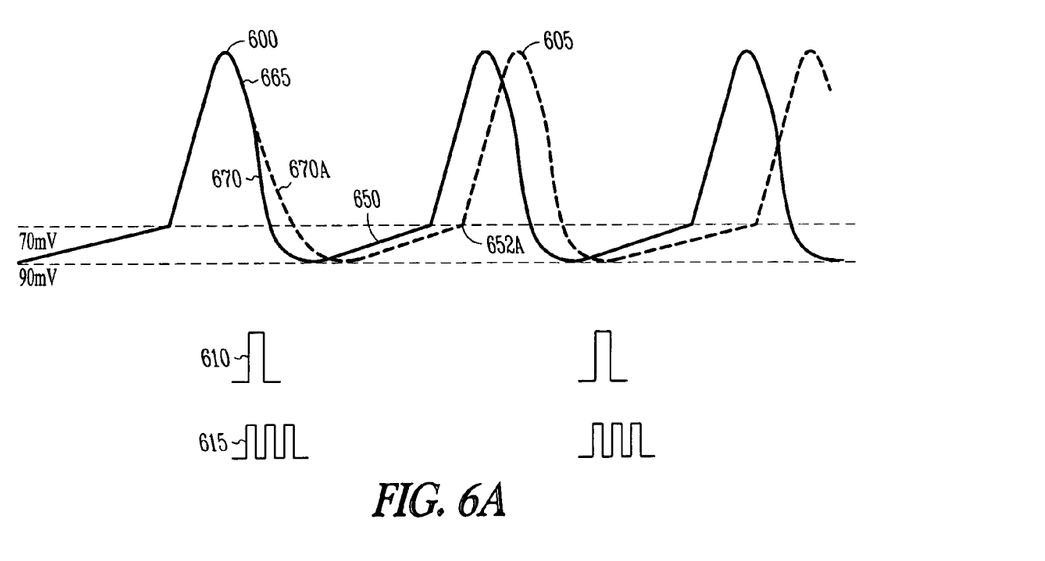
FIGS. 6A and 6B illustrate several sinoatrial cardiac action potentials and examples of inhibitory sinoatrial electrical stimulation.
Figure 6B:
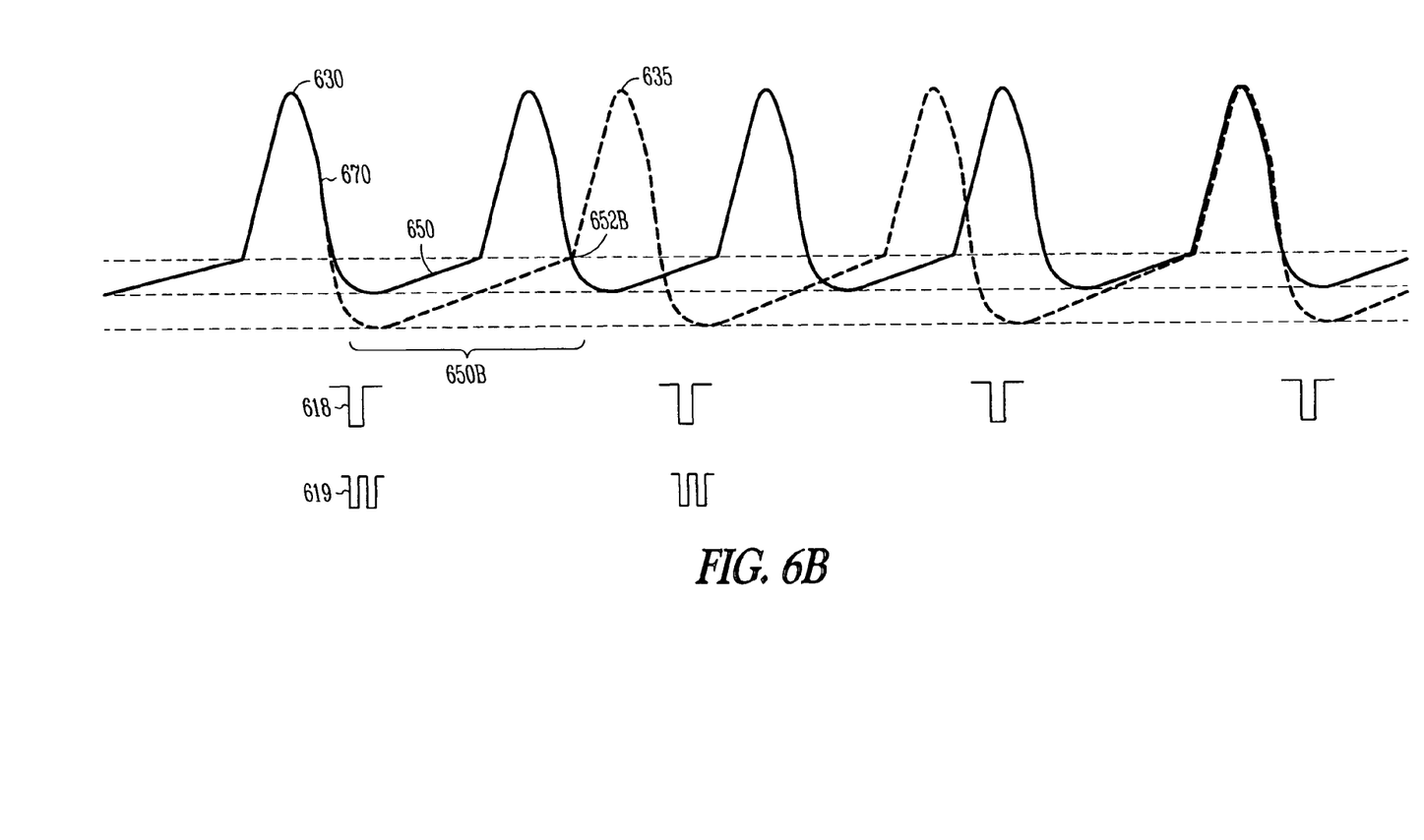

FIGS. 6A and 6B illustrate several sinoatrial cardiac action potentials and examples of inhibitory sinoatrial electrical stimulation. In FIG. 6A, waveform 600 illustrates sinoatrial cardiac action potentials without any alteration. Waveform 605 illustrates a change in the sinoatrial cardiac action potential from waveform 600 due to an electrical stimulation pulse 610 delivered to the sinoatrial node during phase three 670. Electrical stimulation pulse 610 may be a depolarizing pulse. A depolarizing electrical stimulation pulse 610, which may also be referred to as a depolarization-level stimulation pulse, has a sufficient amplitude and pulse-width to normally cause depolarization. In an illustrative example, the amplitude of the depolarization-level pulse may be two millivolts (2 mV). The actual amplitude of the depolarization-level pulse will depend, at least in part, on the proximity of the electrical stimulation electrode to the actual sinoatrial node. If the depolarizing electrical stimulation pulse 610 were delivered during phase four 650 of the sinoatrial cardiac action potential, the depolarizing electrical stimulation pulse 610 would be excitatory and elicit a new action potential at the sinoatrial node (i.e., induce depolarization).

However, because the delivery of the pulse is not during phase four 650, the depolarizing pulse is non-excitatory, i.e., it does not elicit a new action potential at the sinoatrial node. Delivering the depolarizing electrical stimulation pulse 610 during phase three 670 may keep the myocardial cells in depolarization for a longer period of time and may delay repolarization. Waveform 605 shows the effect of the electrical stimulation pulse 610. The electrical stimulation pulse 610 causes a change in phase three 670A. The new phase three 670A has a slower slope causing phase three to be prolonged. This results in a time shift in the sinoatrial cardiac action potential in waveform 605. A longer time is required for the sinoatrial cardiac action potential to reach the firing level 652A. Prolonging phase three lengthens the time duration between sinoatrial cardiac action potentials and reduces the heart rate of a subject.

In some examples, the depolarizing electrical stimulation pulse 610 may be delivered during phase three 670 when the voltage of a sensed sinoatrial cardiac action potential is within a specified threshold of a phase four 650 resting voltage. In an illustrative example, assume the phase four 650 resting voltage is 90 mV. The non-excitatory depolarizing electrical stimulation pulse 610 may be delivered when the sensed sinoatrial cardiac action potential is near the end of phase three 670 and is within a threshold of 20 mV of the resting voltage or 70 mV. This ensures that the non-excitatory depolarizing electrical stimulation pulse 610 is delivered near or substantially at the end of phase three during a relative refractory period. In some examples, if the width of the sinoatrial cardiac action potentials is a consistent value, the depolarizing electrical stimulation pulse 610 may be delivered at a specified time after phase zero is detected.

In some examples, the sinoatrial electrical stimulation may include a burst of depolarizing-level electrical stimulation pulses 610. The amplitude of the pulses in the burst may be smaller than the single electrical stimulation pulse 610. In the example shown, the pulses are delivered during phase three 670. The pulse width of the pulses in the burst may also be smaller. As illustrated in waveform 605, because the burst of depolarizing-level electrical stimulation pulses 615 may lengthen phase three 670, such electrical stimulation may reduce the heart rate. Therefore, such electrical stimulation may also be conceptualized as an inhibitory electrical stimulation.

A depolarizing electrical stimulation pulse 610 or a burst of depolarizing electrical stimulation pulses 615 may be delivered during phase two 665 of a sinoatrial cardiac action potential. Such electrical stimulation may prolong phase two 665 or phase three 670 of a sinoatrial action potential and also reduce heart rate. Therefore, a depolarizing electrical stimulation pulse 610, or a burst of depolarizing electrical stimulation pulses 615, delivered during phase two 665 may also be conceptualized as an inhibitory electrical stimulation.

However, as mentioned previously, if the depolarizing electrical stimulation pulse 610 were delivered during phase four 650 of the sinoatrial cardiac action potential, such an electrical stimulation pulse 610 would induce depolarization and would increase the heart rate of a subject. Thus, such a depolarizing electrical stimulation pulse 610 would be excitatory. However, electrical stimulation delivered during phase four 650 can also be non-excitatory and inhibitory.

FIG. 6B illustrates the effect of sinoatrial electrical stimulation that includes a hyperpolarizing electrical stimulation pulse 618 delivered during phase four 650 of a sinoatrial cardiac action potential to increase the hyperpolarization of the sinoatrial node. Hyperpolarization refers to a shift from the positive to the negative direction of membrane potentials of the sinoatrial cells. In an illustrative example, the amplitude of such a hyperpolarizing pulse 618 may be negative two millivolts (−2 mV). Waveform 630 illustrates sinoatrial cardiac action potentials without any alteration. Waveform 635 shows the effect of the electrical stimulation pulse 610.

The sinoatrial cardiac action potential in waveform 635 exhibits a downward change in the diastolic action potential during the beginning of phase four 650, 650B. This can also be described as a negative shift in the maximal magnitude of the diastolic action potential. The end of phase four 650B is more negative than without the depolarizing electrical stimulation pulse 618. As a result, a longer time is required for the sinoatrial cardiac action potential to reach the firing level 652B and phase four 650B of waveform 635 is lengthened. Lengthening phase four 650B lengthens the time duration between sinoatrial cardiac action potentials and reduces the heart rate of a subject. Thus, the depolarizing electrical stimulation pulse 618 is an inhibitory electrical stimulation pulse. In some examples, a burst of depolarizing electrical stimulation pulses 619 are delivered during phase four 650.

Figure 7:
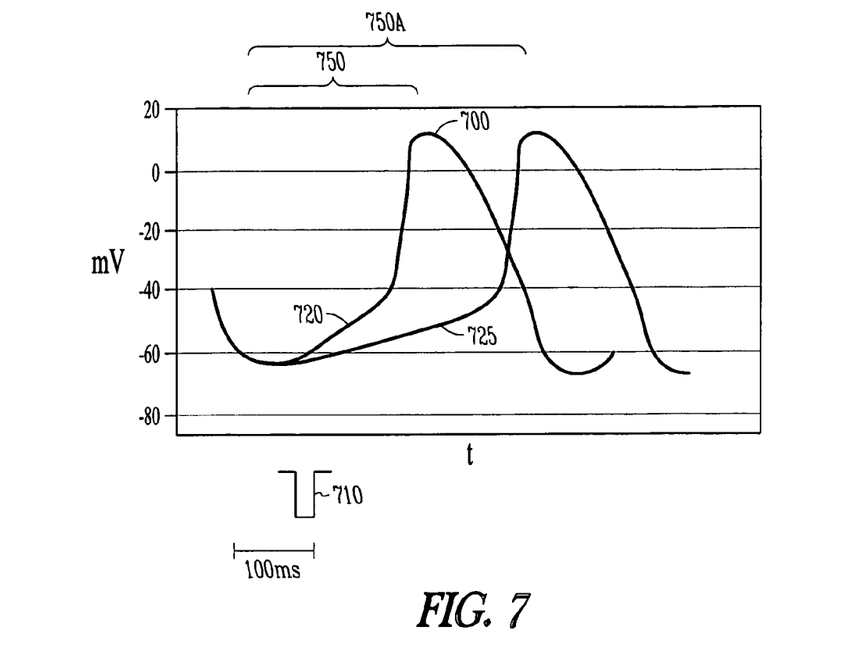
FIG. 7 illustrates another example of inhibitory sinoatrial electrical stimulation.

FIG. 7 illustrates another example of inhibitory sinoatrial electrical stimulation that includes hyperpolarization. The hyperpolarizing electrical stimulation pulse 710 may change the cell conductance, and the slope of the action potential 700 during phase four 750 may be reduced from slope a at 720 to slope b at 725. The reduced slope lengthens phase four 750A. Because phase four 750A is lengthened, the time duration between sinoatrial cardiac action potentials is longer and the heart rate of a subject may be reduced. Delivering electrical stimulation having a negative polarity may include providing cathodal electrical stimulation, such that the stimulation is provided using two electrodes, and the electrode in the vicinity of the sinoatrial node is used as the cathode instead of as the anode.

Figure 8:
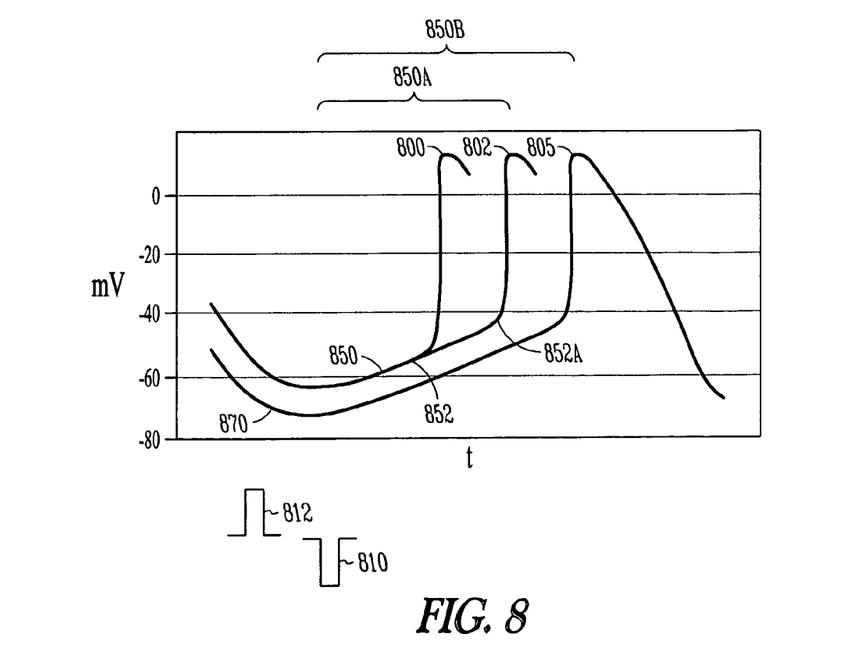
FIG. 8 illustrates yet another example of inhibitory sinoatrial electrical stimulation.

FIG. 8 illustrates another example of inhibitory sinoatrial electrical stimulation. In this example, the inhibitory electrical stimulation includes a hyperpolarizing electrical stimulation pulse 810 delivered during phase four 850 of a sinoatrial cardiac action potential 800. The hyperpolarizing electrical stimulation pulse 810 may change the cell conductance, and the firing threshold level 852 that triggers phase zero depolarization may be increased to a higher (or less negative) level 852A. This lengthens phase four 850A of a sinoatrial cardiac action potential 802, and the heart rate of a subject is reduced.

In some examples, the inhibitory sinoatrial electrical stimulation may include one or more combinations of the electrical stimulations discussed previously. For example, the inhibitory electrical stimulation may include both a depolarizing-level electrical stimulation pulse 812 during the end of phase three 870 and a hyperpolarizing stimulation pulse 810 during phase four 850. Such a combined electrical stimulation may cause any combination of making the slope of phase three 870 to be slower, the beginning of phase four to be more negative, and may increase the firing threshold level 852 to 852A. This may lengthen phase three 870 and phase four 850B of a sinoatrial cardiac action potential 805, and the heart rate of a subject may be reduced further. Other combinations of inhibitory sinoatrial electrical stimulation may include bursts of depolarizing-level pulses, hyperpolarizing pulses, or both depolarizing-level pulses and hyperpolarizing pulses.

Figure 9:
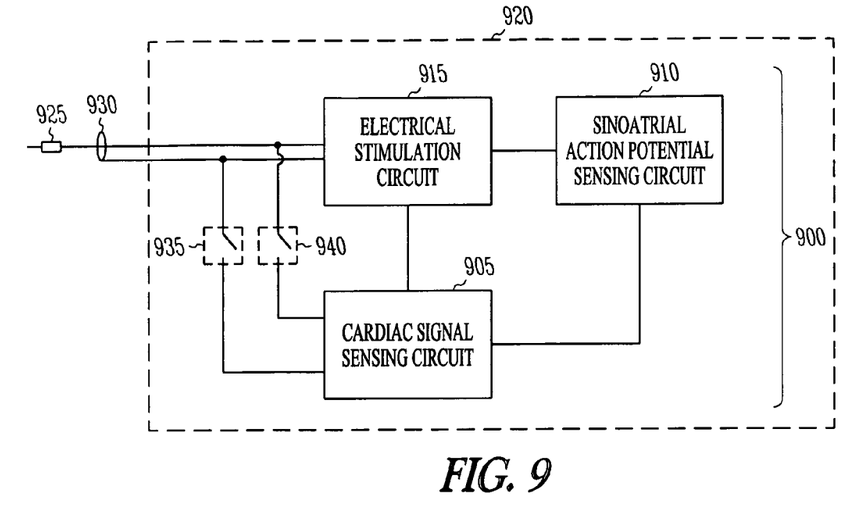
FIG. 9 is a block diagram of portions of an example of a system to provide inhibitory electrical stimulation to a sinoatrial node of a subject.

FIG. 9 is a block diagram of portions of an example of system 900 that is configured to provide inhibitory electrical stimulation to a sinoatrial node of a subject. In this example, the system 900 includes an implantable electrical cardiac signal sensing circuit 905, an implantable sinoatrial cardiac action potential detector circuit 910, and an implantable electrical stimulation circuit 915 that is in electrical communication with the electrical cardiac signal sensing circuit 905 and the sinoatrial cardiac action potential detector circuit 910. In some examples, one or more portions of the system 900 may be included in an IMD 920.

In the example shown, the electrical cardiac signal sensing circuit 905 may receive one or more intrinsic heart signals from one or more respective electrodes configured for placement in a vicinity of a sinoatrial node of a subject. The vicinity of the sinoatrial node may be near a junction between the superior vena cava and the right atrium. The vicinity of the sinoatrial node may be determined using a mapping catheter. In some examples, a mapping catheter includes several electrodes spatially arranged to resemble a basket. The location of the sinoatrial node may be determined from the morphology of electrical activity sensed by the mapping catheter. In some examples, the system 900 includes one or more such implantable electrodes coupled to the electrical stimulation circuit, such as a tip electrode 925 or a ring electrode 930 attached to a cardiac lead, or an electrode located on the IMD 920 can or header.

Returning to FIG. 5, the sinoatrial cardiac action potential detector circuit 910 may identify phase zero 555 from the quick rise in potential, such as by detecting a positive-going change in potential. In some examples, phase zero 555 is detected by measuring a positive-going in potential that exceeds a threshold potential within a specified period of time. An example of a specified period of time is fifty milliseconds (50 ms). Phase four 550 in FIG. 5 may be detected by measuring the resting potential of the sensed sinoatrial cardiac action potentials. In an illustrative example, the resting potential, or lowest potential, in the waveforms may be 90 mV. A substantial end of phase three can be detected when the sensed sinoatrial cardiac action potential is within a threshold of 20 mV of the resting voltage or 70 mV. In some examples, the sinoatrial cardiac action potential detector circuit 910 includes a peak detector, and phase 1 of the sinoatrial cardiac action potentials is detected by detecting the peak of the waveforms. Phase two can be detected when the sensed sinoatrial cardiac action potential is below a threshold value from the peak value.

In some examples, at least a portion of the sinoatrial cardiac action potential detector circuit 910 and at least a portion of the electrical stimulation circuit 915 may include a controller circuit, such as a digital signal processor, application specific integrated circuit (ASIC), microprocessor, or other type of processor, interpreting or executing instructions in software or firmware. In some examples, at least a portion of the electrical stimulation circuit 915 may include at least one software, hardware, or firmware module, or any combination thereof.

The system 900 may include at least one analog to digital converter, such as part of or coupled to either the electrical cardiac signal sensing circuit 905 or the sinoatrial cardiac action potential detector circuit 910 to monitor electrical cardiac signal and detect a sinoatrial cardiac action potential. When a sinoatrial cardiac action potential is detected, the electrical stimulation circuit 915 initiates delivery of at least one inhibitory electrical stimulation pulse in a vicinity of the sinoatrial node in a timed relationship to the sensed sinoatrial cardiac action potential. For example, an electrical stimulation pulse may be delivered in synchrony with a detected phase of a sinoatrial cardiac action potential. In some examples, the system 900 may include one or more switches 935, 940 to disconnect the electrical cardiac signal sensing circuit 905 from sensing electrodes during delivery of the electrical stimulation to protect electronic circuits that may be sensitive to the electrical stimulation.

In some examples, the inhibitory electrical stimulation pulse delivered by the electrical stimulation circuit 915 includes a non-excitatory depolarizing electrical stimulation pulse delivered in the vicinity of the sinoatrial node during a detected phase three of the sensed sinoatrial cardiac action potential. In some examples, the non-excitatory depolarizing electrical stimulation pulse is delivered when a measured voltage of a sensed sinoatrial cardiac action potential is within a specified threshold of a phase four resting voltage. In some examples, the inhibitory electrical stimulation pulse is a non-excitatory depolarizing electrical stimulation pulse delivered during a detected phase two of the sensed sinoatrial cardiac action potential.

In some examples, the electrical stimulation circuit 915 initiates delivery of a plurality of inhibitory electrical stimulation pulses such as a burst of non-excitatory depolarizing electrical stimulation pulses during a detected refractory period of the sinoatrial cardiac action potential, such as during the relative refractory period discussed previously.

In some examples, the inhibitory electrical stimulation pulse delivered by the electrical stimulation circuit 915 includes a hyperpolarizing electrical stimulation pulse delivered during a detected phase four of a sinoatrial cardiac action potential. In some examples, the electrical stimulation circuit 915 delivers inhibitory electrical stimulation that includes one or more combinations of the electrical stimulation pulses and delivery times discussed herein.

Figure 10:
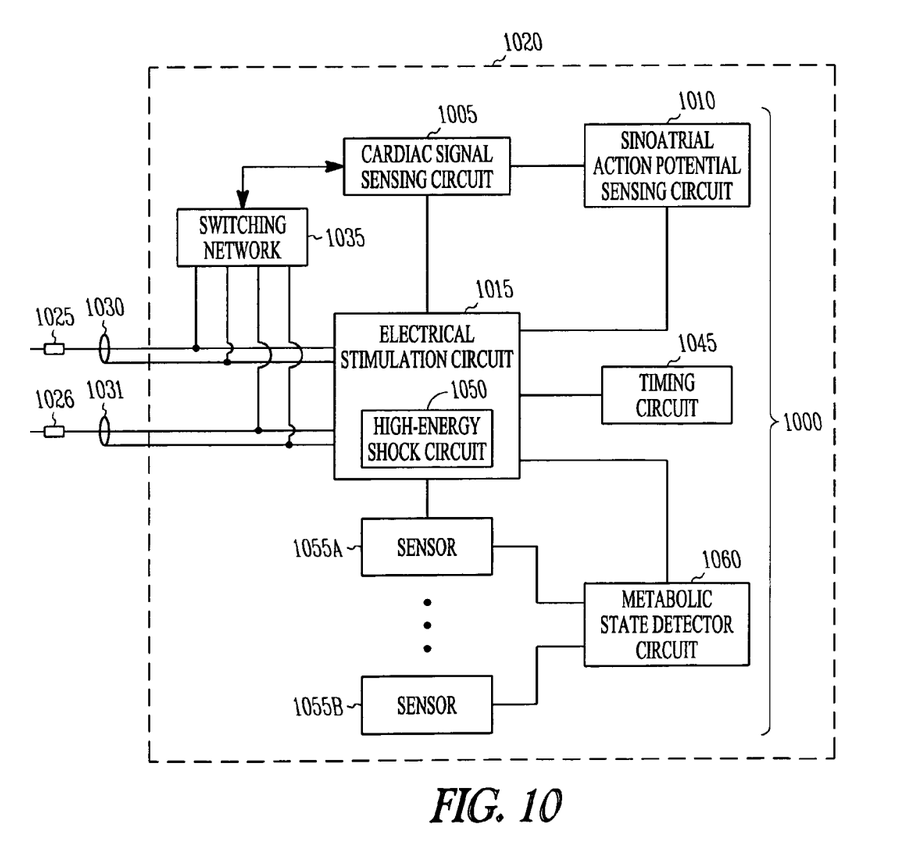
FIG. 10 is a block diagram of portions of another example of a system to provide inhibitory electrical stimulation to a sinoatrial node of a subject.

FIG. 10 is a block diagram of portions of another example of a system 1000 to provide inhibitory electrical stimulation to a sinoatrial node of a subject. In this example, the system 1000 includes an implantable electrical cardiac signal sensing circuit 1005, an implantable sinoatrial cardiac action potential detector circuit 1010, and an implantable electrical stimulation circuit 1015 that is in electrical communication with the electrical cardiac signal sensing circuit 1005 and the sinoatrial cardiac action potential detector circuit 1010. The system 1000 may include or be part of an IMD 1020. The system may include a switching element or network 1035, such as to disconnect the cardiac signal sensing circuit from the sensing electrodes, for example, during a delivered stimulation pulse. The system 1000 may include one or more electrodes configured for placement in a vicinity of a sinoatrial node of a subject, such as tip electrode 1025 or a ring electrode 1030 included with a cardiac lead.

In some examples, the system 1000 includes one or more electrodes configured for placement outside the vicinity of the sinoatrial node, such as tip electrode 1026 or ring electrode 1031 or an electrode included in the IMD 1020 can or header for example. Vicinities within the region of the sinoatrial node include the region of a junction between the superior vena cava and the right atrium. In some examples, vicinities within the region of the sinoatrial node include regions high in the right atrium. Vicinities outside the sinoatrial region include, without limitation, lower regions of the right atrium, regions in or near the left atrium, the ventricles, or the coronary sinus.

The electrodes may be coupled to the electrical stimulation circuit 1015. The electrical the stimulation circuit 1015 adjusts one or more parameters of the one or more electrical stimulations, such as to alter a rate of sinoatrial depolarizations as a function of a heart rate sensed outside the vicinity of the sinoatrial node. For example, the electrical stimulation circuit 1015 may determine that the inhibitory electrical stimulation at the sinoatrial node is not adequately reducing the heart rate of the subject from a signal sensed by an electrode placed in a ventricle.

In some examples, the electrical stimulation circuit 1015 adjusts a pulse parameter such as an amplitude of the pulse or the width of the pulse. If the stimulation is a burst of pulses, the electrical stimulation circuit 1015 may adjust a number of pulses in a burst, a duration of time between pulses in the burst, or may vary the amplitude or pulse-width of pulses within a single burst, such as by ramping or lengthening the pulses, for example.

In some examples, the electrical stimulation circuit 1015 switches between different types of non-excitatory electrical stimulation, such as switching from delivering bursts of smaller amplitude pulses to delivering a single larger amplitude pulse. In some examples, the electrical stimulation circuit 1015 may switch between delivering electrical stimulation between phases two and three of the detected cardiac action potential. In some examples, the electrical stimulation circuit 1015 may switch between delivering a non-excitatory depolarizing pulse during a refractory period of the detected cardiac action potential and delivering a hyperpolarization pulse during phase four of the detected cardiac action potential. In some examples, the electrical stimulation circuit 1015 may apply any combination of the inhibitory electrical stimulation described herein.

In some examples, the electrical stimulation circuit 1015 provides cathodal stimulation. Non-excitatory electrical stimulation energy may be delivered to the vicinity of the sinoatrial node using two electrodes. For example energy can be delivered between a tip electrode 1025 placed in the vicinity of the sinoatrial node and a nearby ring electrode 1030 or an electrode included in the IMD 1020 can or header. In another example, a ring electrode may be placed in the vicinity of the sinoatrial node. In cathodal stimulation, the electrode in the vicinity of the sinoatrial node is the cathode instead of the anode.

In some examples, the electrical stimulation circuit 1015 initiates delivery of a non-excitatory electrical stimulation pulse during the detected sinoatrial cardiac action potential. In some examples, the system 1000 includes a timer circuit 1045 coupled to the electrical stimulation circuit 1015. The detected sinoatrial cardiac action potential is used as a timing reference and the electrical stimulation circuit 1015 initiates delivery on a subsequent sinoatrial cardiac action potential. For example, the sinoatrial cardiac action potential detector circuit 1010 may detect that sinoatrial cardiac action potentials are occurring at a regular rate. In FIG. 6, the electrical stimulation circuit 1015 may deliver a non-excitatory depolarizing electrical stimulation pulse during waveform 602 using waveform 600 or a feature thereof as a timing reference.

According to some examples, inhibitory electrical stimulation can be used to induce bradycardia in patients that may have experienced an episode of myocardial ischemia. Increased heart rate may be a risk factor for patients who have experienced ischemia. As discussed previously, drug therapy such as beta blockers may reduce heart rate but their use may be limited by strong negative effects or contraindications. Also, drug therapy may not target a specific heart rate. The system 900 provides a controllable way to reduce heart rate by reducing the automatic firing frequency of sinus node. The system 900 adds a new capability to low-voltage pacing therapy which traditionally has only been used to increase the heart rate for patients with bradycardia.

Additionally, induced bradycardia may in turn induce the growth of new collateral blood vessels (angiogenesis) in a heart damaged by ischemia. Inhibitory electrical stimulation can be provided to such patients, such as for timed duration each day. Thus, inhibitory electrical stimulation capability can be included in an implantable device to help patients recover from an ischemic episode. In some examples, the IMD 1020 includes an ICD and the electrical stimulation circuit includes an implantable high-energy shock delivery circuit 1050. The electrical stimulation circuit 1015 uses the timer circuit 1045 to recurrently initiate delivery of inhibitory electrical stimulation in a vicinity of the sinoatrial node, such as for a timed duration. For example, the electrical stimulation circuit 1015 may provide inhibitory electrical stimulation to reduce the heart rate of a subject for six or seven hours every day.

In some examples, the system 1000 includes one or more implantable sensors 1055A, 1055B. Each sensor 1055A, 1055B produces an electrical sensor signal related to a physiologic cardiovascular condition of the subject. In some examples, implantable sensor 1055A includes an implantable physical activity sensor in electrical communication with the implantable electrical stimulation circuit 1015. In some examples, the implantable physical activity sensor includes an accelerometer. The electrical stimulation circuit 1015 initiates delivery of the inhibitory electrical stimulation pulse in the vicinity of the sinoatrial node, such as when the physical activity sensor indicates that the subject is at rest. This reduces the subject's resting heart rate.

In some examples, the implantable physical activity sensor is used to provide rate responsive pacing for the subject. The electrical stimulation circuit 1015 may initiate delivery of an excitatory electrical stimulation pulse in the vicinity of the sinoatrial node when the physical activity sensor indicates that the subject is exercising. One or more excitatory electrical stimulation pulses are delivered to increase the heart rate of the subject in response to the detected exercise. The excitatory pulse may be a depolarizing pulse delivered during phase four of a sinoatrial cardiac action potential. Thus, the system 1000 may provide rate adaptive pacing by delivering excitatory electrical stimulation in the vicinity of the sinoatrial node in response to a signal received from the physical activity sensor that indicates the subject is exercising.

In some examples, the rate adaptive electrical stimulation is delivered outside the vicinity of the sinoatrial node region. The electrical stimulation circuit 1015 may initiate delivery of the inhibitory electrical stimulation pulse in the vicinity of the sinoatrial node region to lower heart rate when the activity sensor indicates that the subject is at rest. If the activity sensor indicates the subject is exercising, the electrical stimulation circuit 1015 may initiate delivery of excitatory electrical stimulation to a cardiac region outside of the vicinity of the sinoatrial node region to increase heart rate.

In some examples, the system 1000 includes a metabolic state detector circuit 1060 coupled to the electrical stimulation circuit 1015 and one or more implantable sensors 1055A, 1055B. In some examples, the implantable sensors 1055A, 1055B include a heart sound sensor. Monitoring heart sounds can be used to assess the hemodynamic performance of a subject. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole.

A heart sound sensor produces an electrical signal which is representative of mechanical activity of a patient's heart. The heart sound sensor is disposed in a heart, or near the heart in a location where the acoustic energy can be sensed. In some examples, the heart sound sensor includes an accelerometer disposed in or near a heart. In another embodiment, the heart sound sensor includes a microphone disposed in or near a heart. An approach for monitoring heart sounds is found in Siejko et al., U.S. Patent Application Publ. No. 2004/0127792, entitled "Method and Apparatus for Monitoring of Diastolic Hemodynamics," filed Dec. 30, 2002, which is incorporated herein by reference in its entirety, including its description of monitoring heart sounds. The heart sounds may be used to assess the hemodynamic performance of the subject, such as by using a measure of the strength of one or more heart sounds or the duration of a heart sound. If a heart sound sensor indicates the subject is in a low metabolic state, the electrical stimulation circuit 1015 may initiate delivery of the inhibitory electrical stimulation pulse in the vicinity of the sinoatrial node region to the lower heart rate of the subject.

In some examples, the implantable sensors 1055A, 1055B include an implantable cardiac blood pressure sensor, which can detect a change in left ventricle filling pressure. In some examples, the implantable sensors 1055A, 1055B include an implantable cardiac pressure sensor to measure chamber pressure of the left ventricle. In some examples, the implantable sensors 1055A, 1055B include a pressure sensor to be implanted in a coronary vessel to determine left ventricle pressure by direct measurement of coronary vessel pressure. A description of systems and methods that use an implantable pressure sensor is found in Salo et al., U.S. Pat. No. 6,666,826, entitled "Method and Apparatus for Measuring Left Ventricular Pressure," filed Jan. 4, 2002, which is incorporated herein by reference in its entirety, including its description of using an implantable pressure sensor. Other cardiac pressure sensors examples include a right ventricle (RV) chamber pressure sensor, a pulmonary artery pressure sensor, and a left atrial chamber pressure sensor.

A measure of chamber pressure may be used to assess the hemodynamic performance of the subject, such as by using a measure of strength of contractions of the subject or of the contraction rate. If a cardiac blood pressure sensor indicates the subject is in a low metabolic state, the electrical stimulation circuit 1015 may initiate delivery of the inhibitory electrical stimulation pulse in the vicinity of the sinoatrial node region to the lower heart rate of the subject.

In some examples, the implantable sensors 1055A, 1055B include an impedance sensor. A cardiac impedance sensor senses an electrical impedance signal between electrodes interposed in the heart. For example, in FIG. 2 a cardiac impedance sensor can sense intracardiac impedance of the right ventricle 205A between an electrode placed at the apex of the right ventricle 205A and an electrode placed in the right atrium 200A. A predetermined excitation current is delivered between the electrodes and the impedance is determined from a voltage sensed between the electrodes. A transthoracic impedance of a subject can be measured between the ring electrode 225 and can electrode 250 or header electrode 260. A transthoracic impedance sensor may be used to measure minute respiration volume. An approach to measuring transthoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference in its entirety, including its description of measuring transthoracic impedance. A cardiac impedance sensor can be used to track an impedance signal along with cardiac contractions and create a baseline impedance or normal impedance signal pattern.

An intracardiac impedance waveform can be signal processed to obtain a measure of the time interval beginning with a paced or spontaneous QRS complex (systole marker) and ending with a point where the impedance signal crosses the zero axis in the positive direction following the QRS complex. The resulting time interval is inversely proportional to the contractility of the heart. Systems and methods to measure intracardiac impedance are described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference.

A measure transthoracic impedance or intracardiac impedance may be used to assess the hemodynamic performance of the subject. Transthoracic impedance can be used to monitor respiration and a low respiration rate may indicate that a subject is in a low metabolic state. Intracardiac impedance can be used to monitor contractility of the heart. If an impedance sensor indicates the subject is in a low metabolic state, the electrical stimulation circuit 1015 may initiate delivery of the inhibitory electrical stimulation pulse in the vicinity of the sinoatrial node region to the lower heart rate of the subject.

In some examples, the implantable sensors 1055A, 1055B include an implantable oxygen saturation sensor. An oxygen saturation sensor produces an electrical sensor signal related to changes in the fluid oxygen saturation associated with the heart's mechanical activity, contractility, and blood flow. An approach for using an implantable sensor to measure blood oxygen saturation levels is found in Thompson, U.S. Pat. No. 5,342,406, entitled "Oxygen Sensor Based Capture Detection for a Pacer," filed Oct. 7, 1992, which is incorporated herein by reference in its entirety, including its description of measuring blood oxygen saturation level. If blood oxygen saturation levels indicate the subject is in a low metabolic state, the electrical stimulation circuit 1015 may initiate delivery of the inhibitory electrical stimulation pulse in the vicinity of the sinoatrial node region to the lower heart rate of the subject.

In some examples, the implantable sensors 1055A, 1055B include an implantable chemical sensor. An increase in blood lactic acid level is accompanied by a decrease in blood pH that is detectable with a chemical sensor. An approach to providing a chemical sensor in a coronary sinus is found in Kane et al., U.S. patent application Ser. No. 11/383,933, entitled, "Implantable Medical Device with Chemical Sensor and Related Methods, filed May 17, 2006, which is incorporated herein by reference in its entirety, including its description of chemical sensors and related methods. If sensed blood pH indicates that the subject is in a low metabolic state, the electrical stimulation circuit 1015 may initiate delivery of the inhibitory electrical stimulation pulse in the vicinity of the sinoatrial node region to the lower heart rate of the subject.

In some examples, the metabolic state detector circuit 1060 uses one or more electrical sensor signals provided by the implantable sensors to assess the metabolic state of the subject. The indications resulting from the signals provided by the sensors may be combined according to one or more rules to assess the metabolic state. For example, the indications may be weighted according to how reliably they assess the metabolic state of a subject.

The electrical stimulation circuit 1015 is configured to initiate delivery of inhibitory electrical stimulation pulses in the vicinity of the sinoatrial node when the metabolic state detector circuit detects that the subject is in a state of low metabolic need, i.e., that the subject's metabolic need can be met by a resting heart rate, or a rate lower than the current resting heart rate. If the metabolic state detector circuit 1060 detects that the condition of the subject is deteriorating due to an increased indication of bradycardia, the electrical stimulation circuit 1015 reduces the inhibitory electrical stimulation in the vicinity of the sinoatrial node. In some examples, the inhibitory electrical stimulation is given for a shorter duration. In some examples, the inhibitory electrical stimulation is given less often. In some examples, the inhibitory electrical stimulation is stopped. In some examples, if the metabolic state detector circuit 1060 detects an increased indication of bradycardia, the electrical stimulation circuit 1015 initiates delivery of at least one excitatory electrical stimulation pulse.

Figure 11:
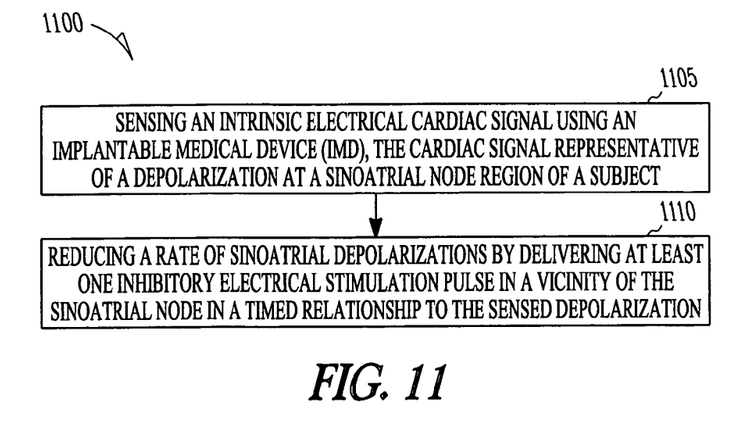
FIG. 11 is a flow diagram of an example of a method for adjusting heart rate.

FIG. 11 is a flow diagram of an example of a method 1100 for adjusting heart rate. At block 1105, an intrinsic electrical cardiac signal is sensed using an implantable medical device (IMD). The sensed cardiac signal is representative of a depolarization at a sinoatrial node region of a subject. At block 1110, the IMD is used to reduce a rate of sinoatrial depolarizations by delivering at least one inhibitory electrical stimulation pulse in a vicinity of the sinoatrial node.

To sense a cardiac signal representative of a depolarization at a sinoatrial node region, the vicinity of the sinoatrial node of a subject is determined. In some examples, this includes using a mapping catheter to locate the vicinity of the sinoatrial node. At least one implantable electrode is placed in the vicinity of the sinoatrial node.

In some examples, sensing the cardiac signal includes sensing one or more phases of a sinoatrial cardiac action potential. The inhibitory electrical stimulation pulse is delivered in a timed relationship to the sensed depolarization, such as in synchrony with one or phases of the sinoatrial cardiac action potential. The inhibitory electrical stimulation pulse may include delivering at least one depolarization-level stimulation pulse during phase three of the sinoatrial cardiac action potential. In some examples, the depolarization-level stimulation pulse is delivered substantially near an end of a phase three. In some examples, near the end of phase three includes being within a specified threshold voltage from the phase four resting voltage. In some examples, near the end of phase three includes a timed duration measured from a detected phase zero.

In some examples, delivering the inhibitory electrical stimulation pulse includes delivering at least one depolarizing-level stimulation pulse during a phase two of the sinoatrial cardiac action potential. In some examples, the inhibitory electrical stimulation pulse includes delivering a hyperpolarizing stimulation pulse during a phase four of the sinoatrial cardiac action potential. In some examples, delivering the at least one inhibitory electrical stimulation pulse includes delivering a burst of depolarizing stimulation pulses during the sinoatrial node refractory period. In some examples, the inhibitory electrical stimulation pulse includes delivering a cathodal electrical stimulation.

In some examples, the rate of sinoatrial depolarizations is reduced by delivering at least one inhibitory electrical stimulation pulse to a vicinity of the sinoatrial node in a timed relationship to the sensed depolarization and increasing a threshold pre-potential that triggers a sinoatrial cardiac action potential. In some examples, delivering the inhibitory electrical stimulation pulse reduces the rate of sinoatrial depolarizations by increasing a threshold pre-potential that triggers a sinoatrial cardiac action potential. In some examples, delivering the inhibitory electrical stimulation pulse reduces the rate of sinoatrial depolarizations by reducing a slope of phase four of a sinoatrial cardiac action potential. In some examples, the inhibitory electrical stimulation pulse reduces the rate of sinoatrial depolarizations by changing a diastolic potential.

In some examples, reducing a rate of sinoatrial depolarizations includes reducing a resting heart rate. In some examples, the method 1100 includes recurrently delivering inhibitory electrical stimulation pulses to a vicinity of the sinoatrial node in a timed duration. The inhibitory electrical stimulation may be used to induce bradycardia in patients that may have experienced an episode of myocardial ischemia. Inhibitory electrical stimulation may help patients recover from an ischemic episode inducing the growth of new collateral blood vessels (angiogenesis) in a heart damaged by ischemia.

In some examples, the method 1100 includes delivering at least one excitatory electrical stimulation pulse in a vicinity of the sinoatrial node region to increase a heart rate when the subject is detected to be exercising. In some examples, the method 1100 includes delivering at least one excitatory electrical stimulation pulse outside of the vicinity of the sinoatrial node region to increase a heart rate when the subject is exercising. The excitatory stimulation outside of the vicinity of the sinoatrial node region may be delivered as an alternative excitatory stimulation or delivered in combination with the excitatory stimulation within the vicinity of the sinoatrial node region. However, the excitatory stimulation within the vicinity of the sinoatrial node region may be sufficient to stimulate the ventricles and additional ventricular pacing may be avoided.

Figure 12:
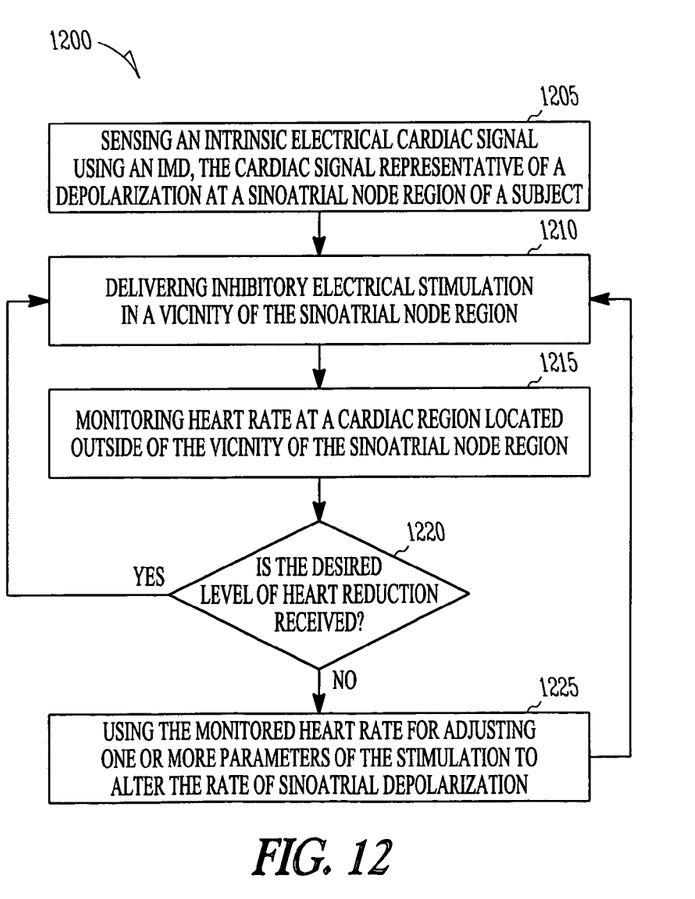
FIG. 12 is a flow diagram of another example of a method for adjusting heart rate.

FIG. 12 illustrates another example of a method 1200 for adjusting heart rate. At 1205, an intrinsic electrical cardiac signal is sensed using an implantable medical device (IMD). The sensed cardiac signal is representative of a depolarization at a sinoatrial node region of a subject. At 1210, inhibitory electrical stimulation is delivered in a vicinity of the sinoatrial node region. At 1215, heart rate is monitored at a cardiac region located outside of the vicinity of the sinoatrial node region. As an illustrative example, heart rate could be monitored by monitoring depolarizations in the right ventricle. At 1220, it is determined whether the inhibitory stimulation achieved the desired reduction in heart rate. If it does, the method 1200 includes continuing to deliver the programmed inhibitory electrical stimulation. If it does not, at 1225, the monitored heart rate is used to adjust one or more parameters of the stimulating in the vicinity of the sinoatrial node to alter the rate of sinoatrial depolarization.

In some examples, a pulse parameter such as an amplitude of the pulse or the width of the pulse may be adjusted. If the stimulation is a burst of pulses, the number of pulses in a burst, a duration of time between pulses in the burst, or the amplitude of pulses within a single burst may be adjusted. In some examples, the type of non-excitatory electrical stimulation is changed among any of the types of non-excitatory electrical stimulation described herein.

Figure 13:
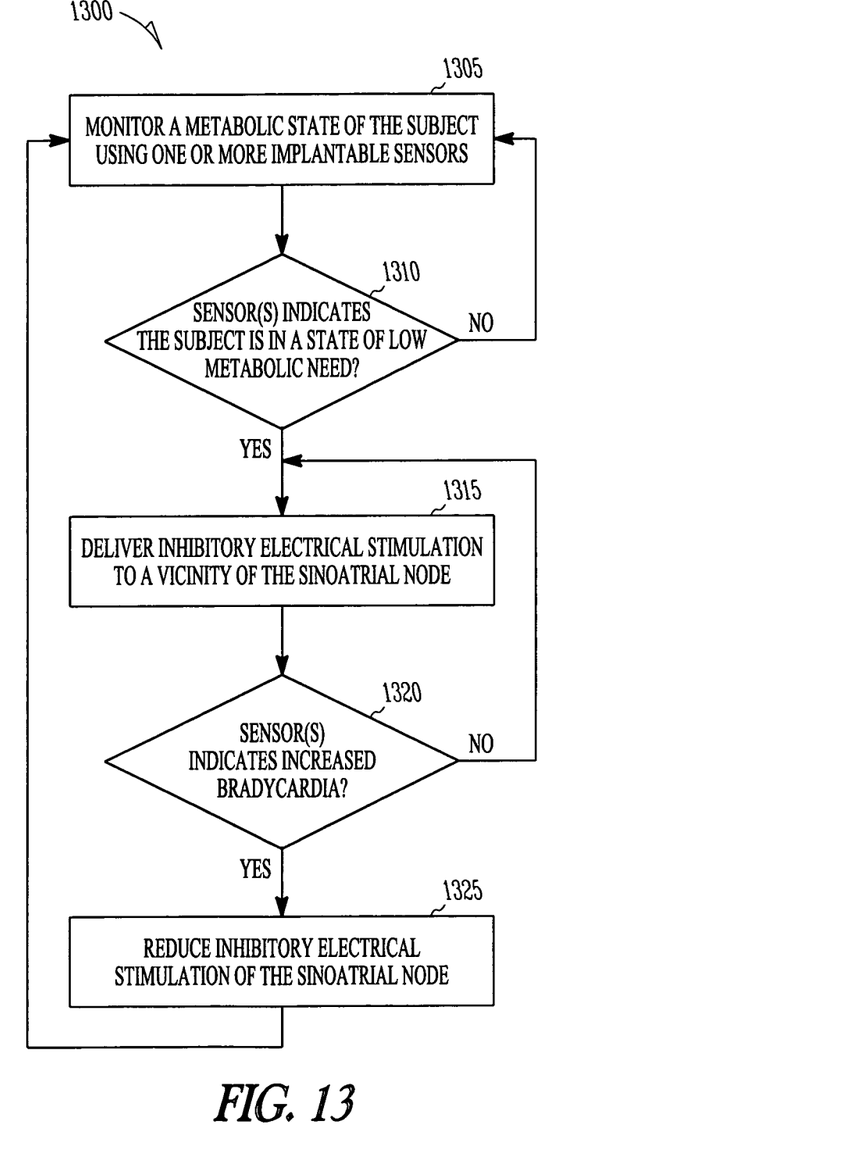
FIG. 13 is a flow diagram of yet another example of a method for adjusting heart rate.

FIG. 13 is a flow diagram of another example of a method 1300 for adjusting heart rate. At block 1305, a metabolic state of the subject is monitored using one or more implantable sensors. Each sensor produces an electrical sensor signal related to a physiologic cardiovascular condition of the subject. In some examples, the implantable sensors include at least one of a heart sound sensor, a cardiac blood pressure sensor, a transthoracic impedance sensor, an intracardiac impedance sensor, a chemical sensor, an oxygen saturation sensor, and an accelerometer.

At block 1310, it is determined if the sensors indicate that the subject is in a state of low metabolic need. If not, the sensor or sensors are monitored. If the subject is in a state of low metabolic need, inhibitory electrical stimulation is delivered in a vicinity of the sinoatrial node to reduce a rate of sinoatrial depolarizations at block 1315. The inhibitory electrical stimulation is delivered in a timed relationship to a cardiac signal sensed in the vicinity of the sinoatrial node. The sensors continue to monitor the subject's condition. At block 1320, it is determined whether a sensor indicates increased bradycardia. If not, the inhibitory electrical stimulation is continued. If the sensor indicates increased bradycardia, the inhibitory electrical stimulation is reduced. In some examples, the inhibitory electrical stimulation may be reduced by being given for a shorter duration. In some examples, the inhibitory electrical stimulation may be given less often. In some examples, the inhibitory electrical stimulation may be stopped.

In some examples, the method 1300 includes delivering at least one excitatory electrical stimulation pulse to a vicinity of the sinoatrial node when the one or more sensors indicate increased bradycardia. In some examples, the method 1300 includes delivering at least one excitatory electrical stimulation pulse to a region outside the sinoatrial node to induce depolarization when the one or more sensors indicate increased bradycardia.

The systems and methods described herein may be used to provide a target low resting heart rate for a subject and can also provide depolarizing pacing to increase the heart rate, such as for rate responsive pacing for exercise for example. This is in contrast to drug therapy such as beta-blockers. Drug therapy may reduce heart rate, but may not selectively increase heart rate. Additionally, drug therapy may not target a specific heart rate or change the target rate. Further, if a subject-patient already has an IMD, negative side-effects from drug therapy such as beta blockers can be avoided by using the IMD to reduce heart rate.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising:
   an implantable electrical cardiac signal sensing circuit configured to receive one or more intrinsic heart signals from one or more respective electrodes configured for placement in a vicinity of a sinoatrial node of a subject;
   an implantable sinoatrial cardiac action potential detector circuit; and
   an implantable electrical stimulation circuit in electrical communication with the electrical cardiac signal sensing circuit and the sinoatrial cardiac action potential detector circuit, wherein the stimulation circuit is configured to initiate delivery of at least one inhibitory electrical stimulation pulse in the vicinity of the sinoatrial node at a specified time relative to a sensed sinoatrial cardiac action potential.

2. The system of claim 1, wherein the stimulation circuit is configured to initiate delivery of at least one non-excitatory depolarizing electrical stimulation pulse in the vicinity of the sinoatrial node in response to the sinoatrial cardiac action potential detector circuit detecting a phase three of the sensed sinoatrial cardiac action potential.

3. The system of claim 2, wherein the stimulation circuit is configured to initiate delivery of at least one non-excitatory depolarizing electrical stimulation pulse in the vicinity of the sinoatrial node during the detected phase three when a measured voltage of a sensed sinoatrial cardiac action potential is within a specified threshold of a resting voltage.

4. The system of claim 1, wherein the sinoatrial cardiac action potential circuit is configured to detect a phase two of the sensed sinoatrial cardiac action potential, and wherein the stimulation circuit is configured to initiate delivery of at least one non-excitatory depolarizing electrical stimulation pulse in response to the sinoatrial cardiac action potential detector circuit detecting a phase two of the sensed sinoatrial cardiac action potential.

5. The system of claim 1, wherein the stimulation circuit is configured to initiate delivery of a burst of non-excitatory depolarizing electrical stimulation pulses in response to the sinoatrial cardiac action potential detector circuit detecting a refractory period of the sinoatrial cardiac action potential.

6. The system of claim 1, wherein the stimulation circuit is configured to initiate delivery of at least one hyperpolarizing electrical stimulation pulse in response to the sinoatrial cardiac action potential detector circuit detecting a phase four of a sinoatrial cardiac action potential.

7. The system of claim 1, wherein the electrical cardiac signal sensing circuit is configured to be coupled to one or more electrodes configured for placement outside the vicinity of the sinoatrial node of a subject, and wherein the electrical stimulation circuit is configured to adjust one or more parameters of the one or more electrical stimulations to alter a rate of sinoatrial depolarizations as a function of a heart rate sensed outside the vicinity of the sinoatrial node.

8. The system of claim 7, further including one or more implantable electrodes configured for placement outside the vicinity of the sinoatrial node of a subject, the electrodes to be coupled to the electrical stimulation circuit.

9. The system of claim 1, wherein the electrical stimulation circuit includes a cathodal electrical stimulation circuit.

10. The system of claim 1, including an implantable physical activity sensor in electrical communication with the implantable electrical stimulation circuit, wherein the electrical stimulation circuit is configured to initiate delivery of the inhibitory electrical stimulation pulse in the vicinity of the sinoatrial node when the activity sensor indicates that the subject is at rest.

11. The system of claim 10, wherein the stimulation circuit is configured to initiate delivery of at least one excitatory electrical stimulation pulse in the vicinity of the sinoatrial node when the activity sensor indicates that the subject is exercising.

12. The system of claim 10, wherein the electrical stimulation circuit is configured to be coupled to at least one electrode configured for placement outside the vicinity of the sinoatrial node of a subject, and wherein the electrical stimulation circuit is configured to initiate delivery of the inhibitory electrical stimulation pulse in the vicinity of the sinoatrial node when the activity sensor indicates that the subject is at rest and to initiate delivery of an excitatory electrical stimulation pulse to a cardiac region outside of the vicinity of the sinoatrial node when the activity sensor indicates the subject is exercising.

13. The system of claim 12, further including one or more implantable electrodes configured for placement outside the vicinity of the sinoatrial node of a subject, the electrodes to be coupled to the electrical stimulation circuit.

14. The system of claim 1, including a timer circuit coupled to the electrical stimulation circuit, wherein the stimulation circuit is configured to recurrently initiate delivery of inhibitory electrical stimulation in a vicinity of the sinoatrial node for a timed duration.

15. The system of claim 14, wherein the electrical stimulation circuit includes an implantable high-energy shock delivery circuit coupled to the implantable electrical cardiac signal sensing circuit.

16. The system of claim 1, including:
one or more implantable sensors operable to produce an electrical sensor signal related to a physiologic cardiovascular condition of the subject;
a metabolic state detector circuit, coupled to the electrical stimulation circuit and the implantable sensors; and
wherein the electrical stimulation circuit is configured to initiate delivery of inhibitory electrical stimulation pulses in the vicinity of the sinoatrial node when the metabolic state detector circuit detects that the subject is in a state of low metabolic need and configured to reduce the inhibitory electrical stimulation in the vicinity of the sinoatrial node when the metabolic state detector circuit detects an increased indication of bradycardia.

17. The system of claim 16, wherein the electrical stimulation circuit is configured to initiate delivery of at least one excitatory electrical stimulation pulse when the metabolic state detector circuit detects an increased indication of bradycardia.

18. The system of claim 16, wherein the one or more implantable sensors include one or more sensors from the group consisting of:
a) a heart sound sensor;
b) a cardiac blood pressure sensor;
c) a transthoracic impedance sensor;
d) an intracardiac impedance sensor;
e) a chemical sensor;
f) an oxygen saturation sensor; and
g) an accelerometer.

19. The system of claim 1, further including one or more implantable electrodes for placement in a vicinity of the sinoatrial node of the subject, the electrodes to be coupled to the electrical stimulation circuit.

* * * * *